United States Patent
Baek et al.

(10) Patent No.: US 9,543,363 B2
(45) Date of Patent: Jan. 10, 2017

(54) ORGANIC LIGHT EMITTING DIODE DISPLAY DEVICE

(71) Applicant: SAMSUNG DISPLAY CO., LTD., Yongin, Gyeonggi-Do (KR)

(72) Inventors: Jong-In Baek, Yongin (KR); Won Sang Park, Yongin (KR)

(73) Assignee: Samsung Display Co., Ltd., Yongin, Gyeonggi-do (KR)

( * ) Notice: Subject to any disclaimer, the term of this patent is extended or adjusted under 35 U.S.C. 154(b) by 305 days.

(21) Appl. No.: 14/281,987

(22) Filed: May 20, 2014

(65) Prior Publication Data
US 2014/0353636 A1 Dec. 4, 2014

(30) Foreign Application Priority Data

Jun. 3, 2013 (KR) .................. 10-2013-0063505

(51) Int. Cl.
*H01L 27/32* (2006.01)
*A61N 5/06* (2006.01)

(52) U.S. Cl.
CPC ......... *H01L 27/3213* (2013.01); *A61N 5/0618* (2013.01); *H01L 27/3223* (2013.01); *A61N 2005/0653* (2013.01)

(58) Field of Classification Search
None
See application file for complete search history.

(56) References Cited

U.S. PATENT DOCUMENTS

| 7,896,530 B2* | 3/2011 | Budinger | A61N 5/0618 362/471 |
| 2009/0281604 A1* | 11/2009 | De Boer | A61M 21/00 607/88 |
| 2010/0264850 A1* | 10/2010 | Yamamoto | G09G 5/14 315/312 |
| 2012/0008326 A1* | 1/2012 | Jou | A61M 21/02 362/293 |

(Continued)

FOREIGN PATENT DOCUMENTS

| JP | 2005-063687 A | 3/2005 |
| JP | 4544948 B2 | 7/2010 |
| JP | 2012-009185 A | 1/2012 |

OTHER PUBLICATIONS

George C. Brainard, et al.; Action Spectrum for Melatonin Regulation in Humans: Evidence for a Novel Circadian Photoreceptor; The Journal of Neuroscience, Aug. 15, 2001, pp. 6405-6412.

*Primary Examiner* — Ashok Patel
(74) *Attorney, Agent, or Firm* — Lee & Morse, P.C.

(57) ABSTRACT

A display device includes a first pixel and a second pixel. The second pixel is controlled to emit light in a predetermined range in a first time period and to not emit light in the predetermined range in a second time period during which the first pixel emits light. The first pixel includes a first organic emission layer having a first thickness and the second pixel includes a second organic emission layer having a second thickness different from the first thickness. A resonance pattern is formed in the second pixel to emit light in a melatonin production inhibition wavelength range that corresponds to the predetermined range. The first pixel may emit blue light, green light, red light, or another color of light including white light.

19 Claims, 7 Drawing Sheets

(56) References Cited

U.S. PATENT DOCUMENTS

| | | | | |
|---|---|---|---|---|
| 2013/0301034 | A1* | 11/2013 | Olds | A61N 5/0618 356/51 |
| 2014/0052220 | A1* | 2/2014 | Pedersen | A61N 5/0618 607/88 |
| 2014/0228914 | A1* | 8/2014 | van de Ven | A61N 5/0618 607/88 |
| 2014/0254139 | A1* | 9/2014 | Park | G09G 3/20 362/97.1 |

* cited by examiner

ORGANIC LIGHT EMITTING DIODE DISPLAY DEVICE

CROSS-REFERENCE TO RELATED APPLICATION

Korean Patent Application No. 10-2013-0063505, filed on Jun. 3, 2013, and entitled, "Organic Light Emitting Diode Display," is incorporated by reference herein in its entirety.

BACKGROUND

1. Field

One or more embodiments described herein relate to a display device.

2. Description of the Related Art

Melatonin is a hormone that influences biorhythms (such as circadian rhythm and annual rhythm in reproductive activity) by sensing photoperiods. The secretion of melatonin is controlled by melatonin control cells found in human eyes.

When melatonin control cells absorb light of a melatonin production inhibition wavelength of 446 nm to 477 nm having a peak of 464 nm in sunlight, the melatonin control cell suppresses secretion of melatonin. Thus, in daytime, during which light of the melatonin production inhibition wavelength is irradiated, the production of melatonin is suppressed by the melatonin control cells. As a result, the human body feels less tired. Conversely, in nighttime, during which light of the melatonin production inhibition wavelength is not irradiated, the production of melatonin is not suppressed. As a result, the human body feels tired and needs sleep.

Melatonin affects other biological functions. For example, melatonin influences metabolism related to blood flow, hormone control, and removal of bodily waste.

These days, people tend to stay indoors more during the day, and thus have less chance of being exposed to sunlight including a melatonin production inhibition wavelength. The human body, therefore, may not be able to function under optimum conditions. Also, the production of melatonin may be suppressed late into the night because of watching television or other lighting effects. Consequently, people may not have sound sleep. In an attempt to obtain improved sleep, people may take chemically composed melatonin medications or supplements. However, these medications or supplements have been shown to have deleterious effects.

SUMMARY

In accordance with one or more embodiments, an organic light emitting diode (OLED) display device includes a substrate and three color pixels and a melatonin control pixel on the substrate, wherein the melatonin control pixel emits or blocks light in a melatonin production inhibition wavelength range. The melatonin production inhibition wavelength range may include about 414 nm to about 514 nm. The light emitted from the melatonin control pixel may have a peak in the melatonin production inhibition wavelength range, and may have a full width at half maximum of greater than 1 nm and less than 50 nm.

Each of the three color pixels and the melatonin control pixel may include thin film transistors on the substrate, a first electrode connected to the thin film transistors, an organic emission layer on the first electrode, and a second electrode on the organic emission layer. A thickness of the organic emission layer of one or more of the three color pixels may be different from a thickness of the organic emission layer of the melatonin control pixel. The organic emission layer of the melatonin control pixel may emit the light in the melatonin production inhibition wavelength range. The three color pixels may be a red pixel, a green pixel, and a blue pixel.

In accordance with another embodiment, a display device includes a signal line and a first pixel connected to the signal line, wherein the first pixel is to emit light in a predetermined range during a first time period and is not to emit light in the predetermined range during a second time period during which an image is displayed, wherein the second time period does not overlap the first time period, and wherein the predetermined range is a melatonin production inhibition wavelength range.

The first pixel may receive a control signal from the signal line. The second pixel may emit or may not emit light in the predetermined range based on the control signal. The first time period may be daytime and the second time period may be nighttime.

A plurality of second pixels may emit different colors of light during the first and second time periods. The light emitted from the first pixel may have a peak in the melatonin production inhibition wavelength range, and has a full width at half maximum of greater than 1 nm and less than 50 nm. A sum of light from the first pixel and light from at least one of the second pixels may combine to increase inhibition of production of melatonin in during the first time period. At least one of the second pixels may be a blue pixel.

In accordance with another embodiment, a display device includes a first pixel to emit light; and a second pixel to emit light in a predetermined range in a first time period and to not emit light in the predetermined range in a second time period during which the first pixel emits light, wherein the first pixel includes a first organic emission layer having a first thickness and the second pixel includes a second organic emission layer having a second thickness different from the first thickness, and wherein a resonance pattern is formed in the second pixel to emit light in a melatonin production inhibition wavelength range that corresponds to the predetermined range.

The first time period may be daytime and the second time period may be nighttime. The first pixel may emit blue light. Also, the first pixel may emit light when the second pixel does not emit light in the predetermined range. The light emitted from the first pixel may have a peak in the melatonin production inhibition wavelength range, and may have a full width at half maximum of greater than 1 nm and less than 50 nm. A sum of light from the first pixel and light from the second pixel may combine to increase inhibition of production of melatonin in during the first time period.

DETAILED DESCRIPTION

Figure 1:
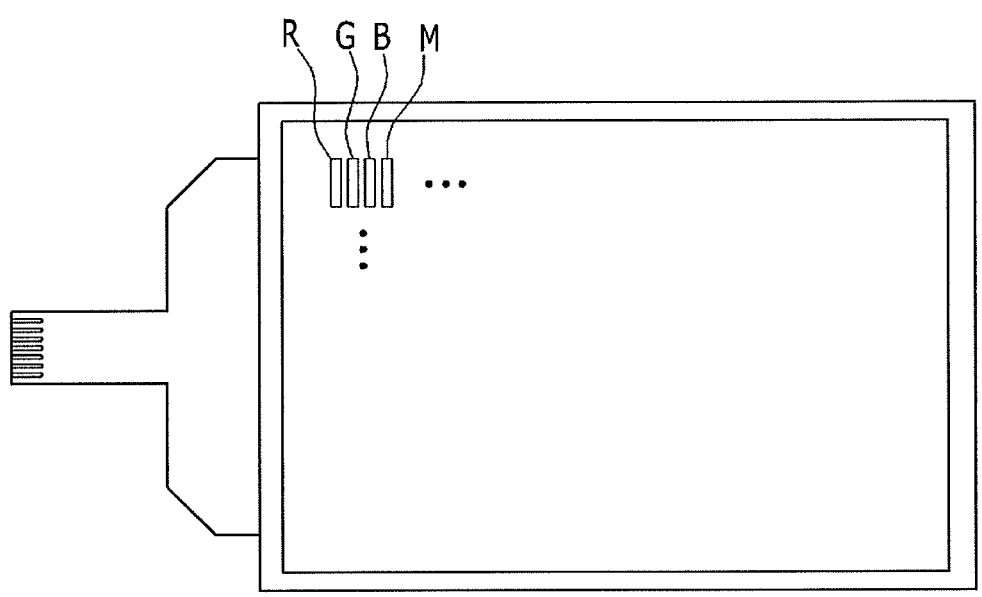
FIG. 1 illustrates an embodiment of a display device.

Example embodiments are described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

Figure 2:
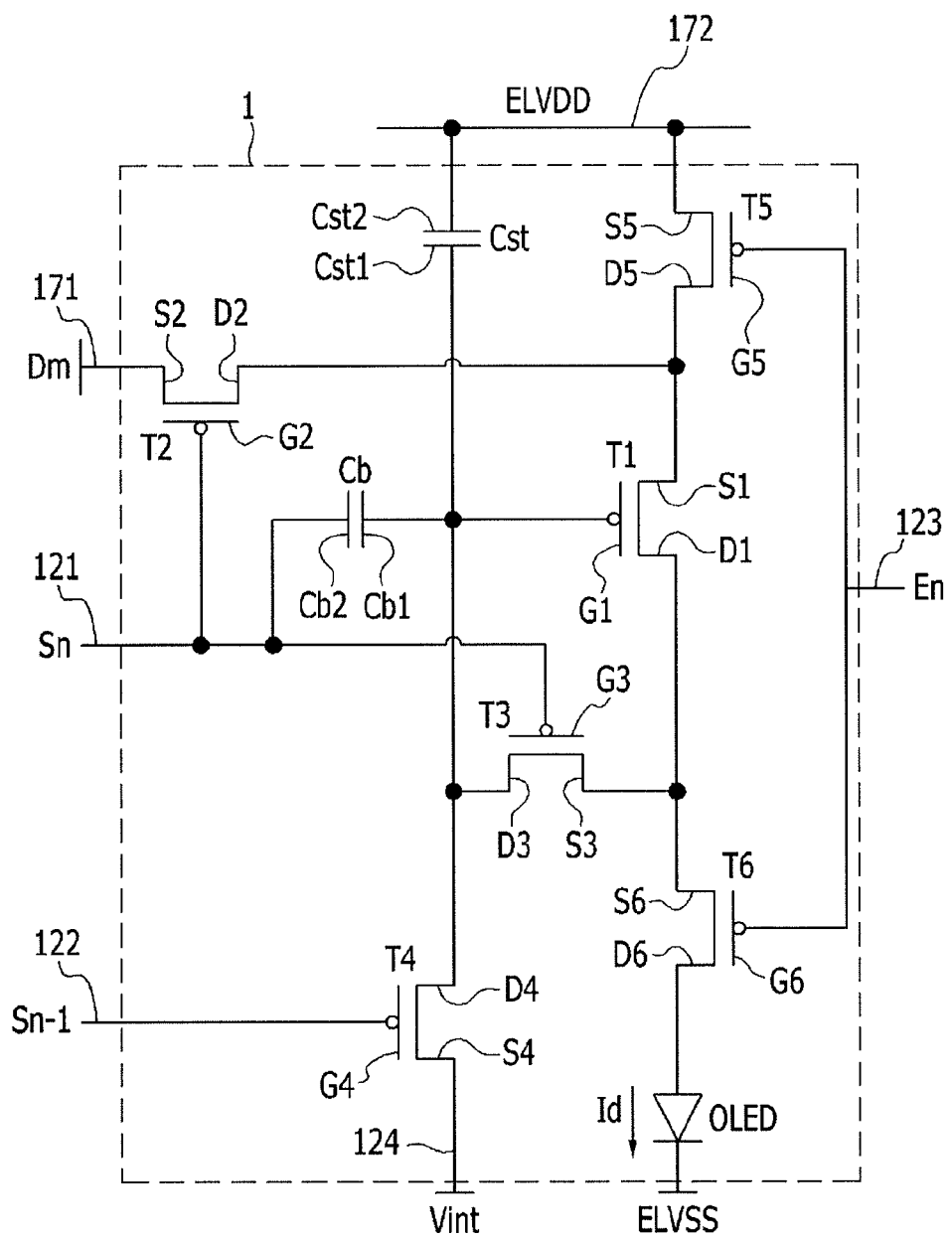
FIG. 2 illustrates an embodiment of a pixel of the display device.

FIG. 1 illustrates an embodiment of an OLED display device, and FIG. 2 illustrates an equivalent circuit diagram of one embodiment of a pixel of this device. As shown in FIG. 1, an OLED display device includes three color pixels and a melatonin control pixel M. The three color pixels include a red pixel R, a green pixel G, and a blue pixel B. The three color pixels emit light to form an image.

The melatonin control pixel emits light in a melatonin production inhibition wavelength range in the daytime and blocks light of the melatonin production inhibition wavelength range in the nighttime. As a result, light emitted from the melatonin control pixel suppresses production of melatonin of a viewer in the day and boosts melatonin production in the night for activation of biorhythms. In one embodiment, the wavelength range of melatonin production suppression may be from 414 nm to 514 nm.

FIG. 2 illustrates one embodiment of a pixel 1 which may correspond to one or more of the three color pixels R, G, and B and the melatonin control pixel M. As illustrated in FIG. 2, pixel 1 includes a plurality of signal lines 121, 122, 123, 124, 171, and 172, a plurality of thin film transistors T1, T2, T3, T4, T5, and T6, capacitors Cst and Cb, and an organic light emitting diode OLED connected to the plurality of signal lines 121, 122, 123, 124, 171, and 172.

The thin film transistors include a driving thin film transistor T1, a switching thin film transistor T2, a compensation thin film transistor T3, an initialization thin film transistor T4, an operation control thin film transistor T5, and a light emission control thin film transistor T6. Capacitor Cst may be a storage capacitor and capacitor Cb may be a boosting capacitor.

The signal lines may include a scan line 121 transmitting a scan signal Sn, a previous scan line 122 transmitting a previous scan signal Sn−1 to the initialization thin film transistor T4, a light emission control signal line 123 transmitting a light emission control signal En to the operation control thin film transistor T5 and the light emission control thin film transistor T6, a data line 171 crossing the scan line 121 and transmitting a data signal Dm, a driving voltage line 172 transmitting a driving voltage ELVDD and formed substantially in parallel with the data line 171, and an initialization voltage line 124 transmitting an initialization voltage Vint that initializes the driving thin film transistor T1.

A gate electrode G1 of the driving thin film transistor T1 is connected to a first end of storage capacitor Cst. A source electrode S1 of the driving thin film transistor T1 is connected to the driving voltage line 172, via the operation control thin film transistor T5. A drain electrode D1 of the driving thin film transistor T1 is electrically connected to an anode of the organic light emitting diode OLED, via the light emission control thin film transistor T6. The driving thin film transistor T1 receives data signal Dm according to a switching operation of the switching thin film transistor T2, and supplies a driving current Id to the organic light emitting diode OLED.

A gate electrode G2 of the switching thin film transistor T2 is connected to the scan line 121, a second end Cb2 of the boosting capacitor Cb, and a gate electrode G3 of the compensation thin film transistor T3. A source electrode S2 of the switching thin film transistor T2 is connected to the data line 171. A drain electrode D2 of the switching thin film transistor T2 is connected to the driving voltage line 172, via the operation control thin film transistor T5, and is connected to the source electrode S1 of the driving thin film transistor T1. The switching thin film transistor T2 is turned on according to the scan signal Sn transmitted through the scan line 121. The switching thin film transistor T2 performs a switching operation to transmit data signal Dm from data line 171 to the source electrode S1 of the driving thin film transistor T1.

A gate electrode G3 of the compensation thin film transistor T3 is connected to the scan line 121, the gate electrode G2 of the switching thin film transistor T2, and a second end Cb2 of the boosting capacitor Cb. A source electrode S3 of the compensation thin film transistor T3 is connected to the anode of the organic light emitting diode OLED, via the light emission control thin film transistor T6, and is connected to the drain electrode D1 of the driving thin film transistor T1. A drain electrode D3 of the compensation thin film transistor T3 is connected to the first end Cst1 of the storage capacitor Cst, the first end Cb1 of the boosting capacitor Cb, and a drain electrode D4 of the initialization thin film transistor T4. The compensation thin film transistor T3 is turned on according to the scan signal Sn transmitted through the scan line 121, and thus diode-connects the driving thin film transistor T1 by connecting the gate electrode G1 and the drain electrode D1 of the driving thin film transistor T1.

A gate electrode G4 of the initialization thin film transistor T4 is connected to the previous scan line 122 of the gate electrode G4. A source electrode S4 of the initialization thin film transistor T4 is connected to the initialization voltage line 124. The drain electrode D4 of the initialization thin film transistor T4 is connected to the first end Cb1 of the boosting capacitor Cb, the first end Cst1 of the storage capacitor Cst, the drain electrode D3 of the compensation thin film transistor T3, and the gate electrode G1 of the driving thin film transistor T1.

The initialization thin film transistor T4 is turned on according to the scan signal Sn−1 transmitted through the previous scan line 122, and performs an initialization operation to initialize a voltage of the gate electrode G1 of the driving thin film transistor T1 by transmitting the initialization voltage Vint to the gate electrode G1 of the driving thin film transistor T1.

A gate electrode G5 of the operation control thin film transistor T5 is connected to the light emission control line 123. A source electrode S5 of the operation control thin film transistor T5 is connected to the driving voltage line 172. A drain electrode D5 of the operation control thin film transistor T5 is connected to the source electrode S1 of the driving thin film transistor T1 and the drain electrode S2 of the switching thin film transistor T2.

A gate electrode G6 of the light emission control thin film transistor T6 is connected to the light emission control line 123 A source electrode S6 of the light emission control thin film transistor T6 is connected to the drain electrode D1 of the driving thin film transistor T1 and the source electrode S3 of the compensation thin film transistor T3. A drain electrode D6 of the light emission control thin film transistor T6 is electrically connected to the anode of the organic light emitting diode OLED.

The operation control thin film transistor T5 and the light emission control thin film transistor T6 are turned on according to the light emission control signal En transmitted through the light emission control line 123. The driving voltage ELVDD is transmitted to the organic light emitting diode OLED to allow driving current Id to flow to the organic light emitting diode OLED.

The second end Cst2 of the storage capacitor Cst is connected to the driving voltage line 172. A cathode of the organic light emitting diode OLED is connected to a common voltage ELVSS. Accordingly, the organic light emitting diode OLED emits light based on the driving current Id received from the driving thin film transistor T1 to display an image.

An operation process of the pixel of the OLED display device will now be described. Initially, a low-level previous scan signal Sn−1 is supplied through the previous scan line 122 during an initialization period. Then, the initialization thin film transistor T4 is turned on corresponding to the low-level previous scan line Sn−1. Then, the initialization voltage Vint is connected to the gate electrode G1 of the driving thin film transistor T1 through the initialization thin film transistor T4 from the initialization voltage line 124. As a result, the driving thin film transistor T1 is initialized by the initialization voltage Vint.

Subsequently, a low-level scan signal Sn is supplied through the scan line 121 during a data programming period. Then, the switching thin film transistor T2 and the compensation thin film transistor T3 are turned on in response to the low-level scan signal Sn. In this case, the driving thin film transistor T1 is diode-connected by the turned-on state of the compensation thin film transistor T3, and thus is biased in a forward direction.

Then, a compensation voltage (Dm+Vth, where Vth is a negative value), reduced by a threshold voltage Vth of the driving thin film transistor T1 from the data signal Dm supplied from the data line 171, is applied to the gate electrode G1 of the driving thin film transistor T1.

The driving voltage ELVDD and compensation voltage (Dm+Vth) are applied to respective ends of the storage capacitor Cst. A charge corresponding to a voltage difference between these ends of the storage capacitor Cst is stored in the storage capacitor Cst.

Subsequently, when supply of the scan signal Sn is stopped, and thus a voltage level of the scan signal Sn is changed to high level, a voltage applied to the gate electrode G1 of the driving thin film transistor T1 is changed in response to a voltage change width of the scan signal Sn due to the coupling action of the boosting capacitor Cb. In this case, the voltage applied to the gate electrode G1 of the driving thin film transistor T1 is changed by charge sharing between the storage capacitor Cst and the boosting capacitor Cb. Therefore, a variation amount of a voltage applied to the driving gate electrode G1 is changed in proportion to a charge sharing value between the storage capacitor Cst and the boosting capacitor Cb, in addition to the voltage change width of the scan signal Sn.

Thus, the light emission control signal En supplied from the light emission control line 123 during a light emission period is changed to low level from high level. Then, the operation control thin film transistor T5 and the light emission control thin film transistor T6 are turned on by the low-level light emission control signal En during the light emission period.

The driving current Id is then generated based on a voltage difference between a voltage of the gate electrode G1 of the driving thin film transistor T1 and the driving voltage ELVDD. The driving current Id is supplied to the organic light emitting diode OLED through the light emission control thin film transistor T6. During the light emission period, a gate-source voltage Vgs of the driving thin film transistor T1 is maintained at (Dm+Vth)−ELVDD by the storage capacitor Cst. According to a current-voltage relationship of the driving thin film transistor T1, the driving current Id becomes proportional to the square (i.e., $(Dm-ELVDD)^2$) of the value acquired by subtracting the threshold voltage Vth from the gate-source voltage Vgs. Thus, the driving current Id is determined regardless of the threshold voltage Vth of the driving thin film transistor T1.

Figure 3:
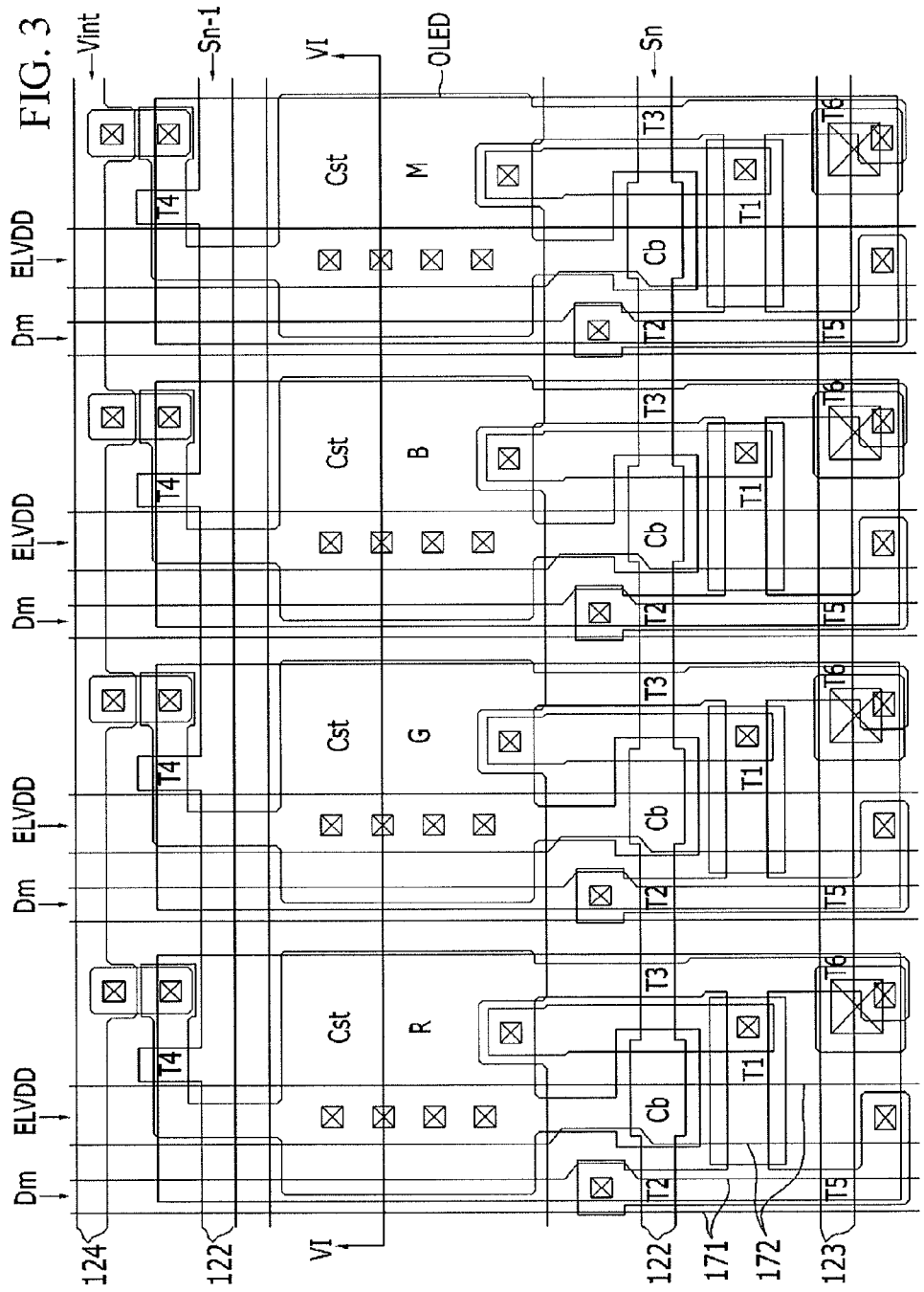
FIG. 3 illustrates a layout for sequentially arranged pixels of the display device.
Figure 4:
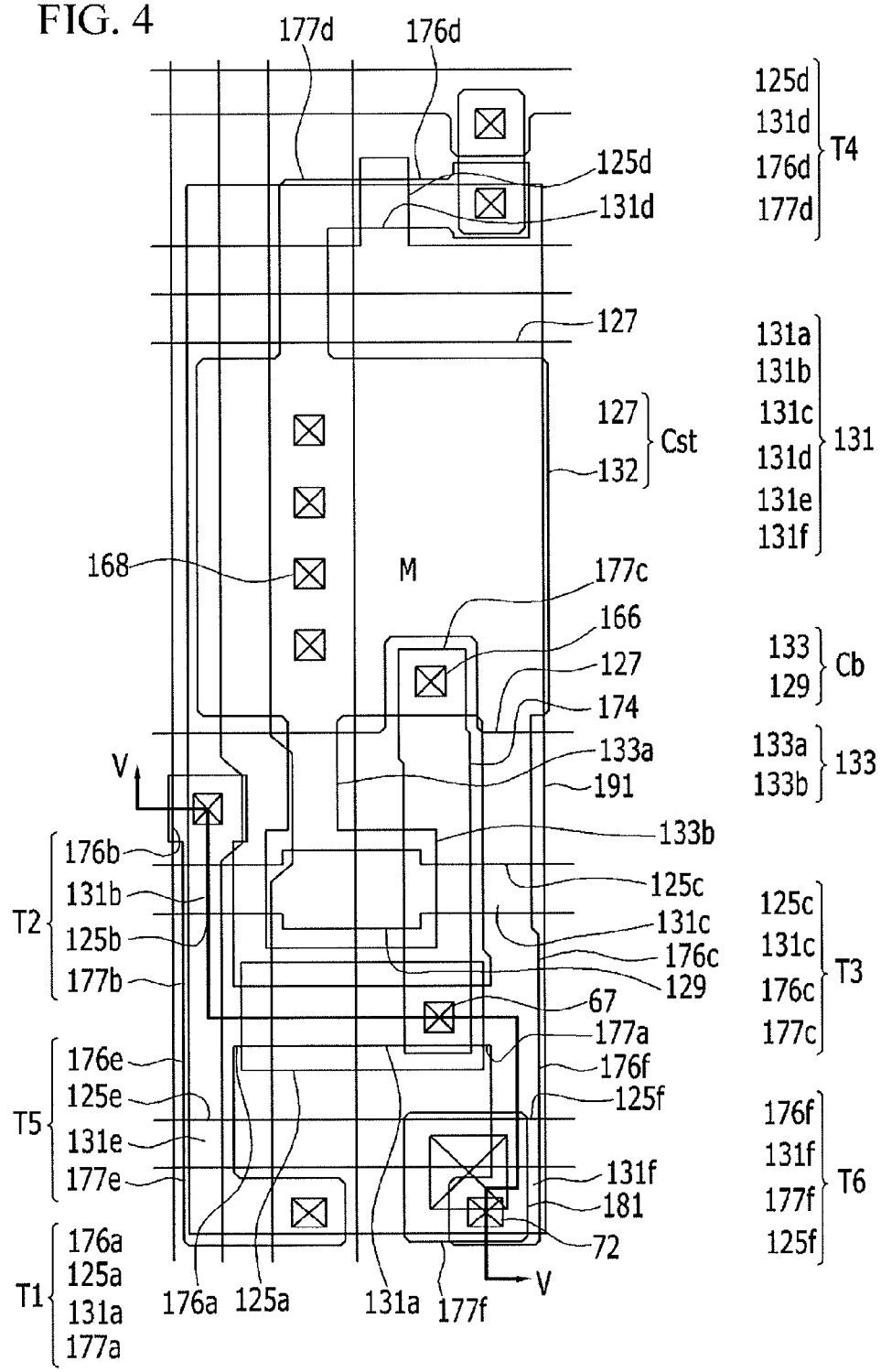
FIG. 4 illustrates a layout of a melatonin control pixel in FIG. 3.
Figure 5:
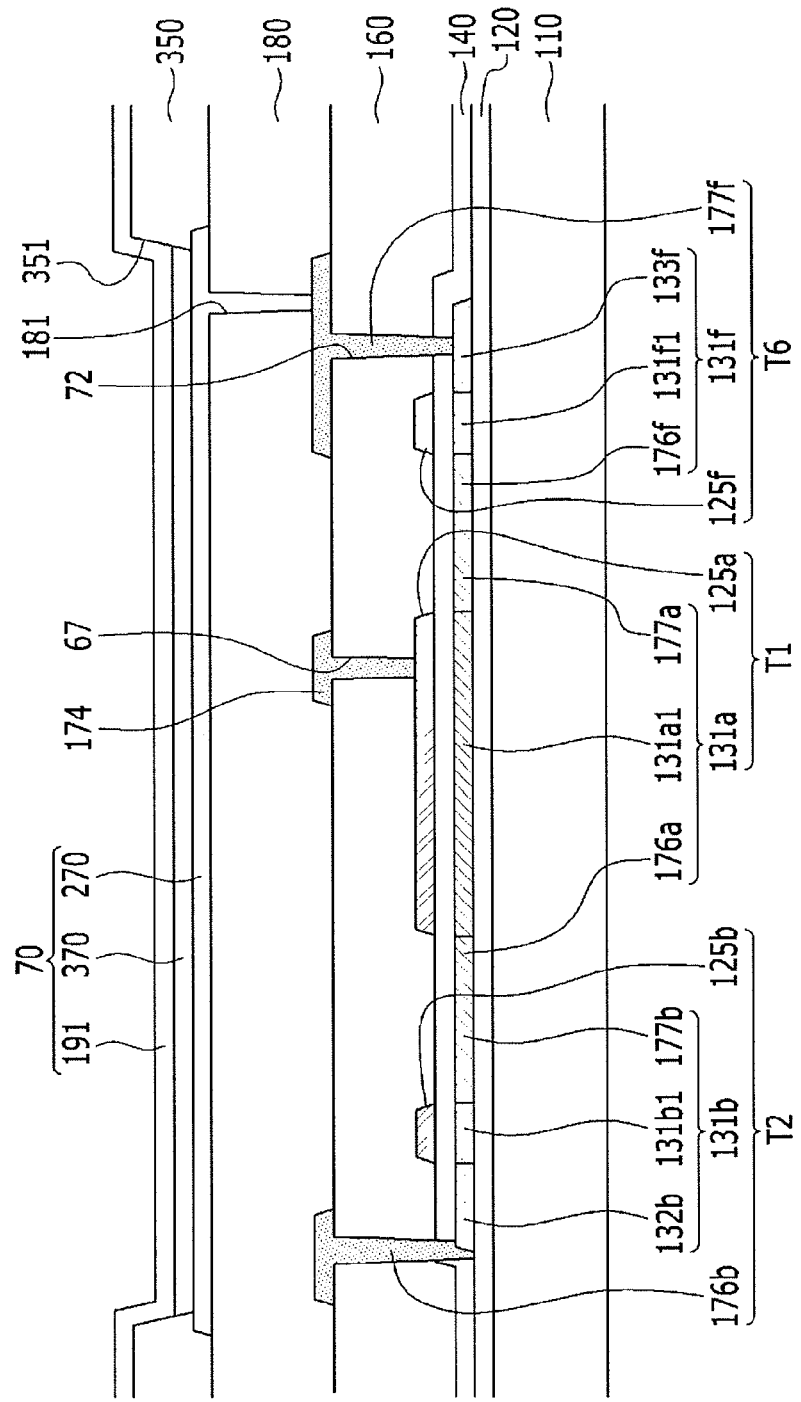
FIG. 5 illustrates a view taken along section line V-V in FIG. 4.
Figure 6:
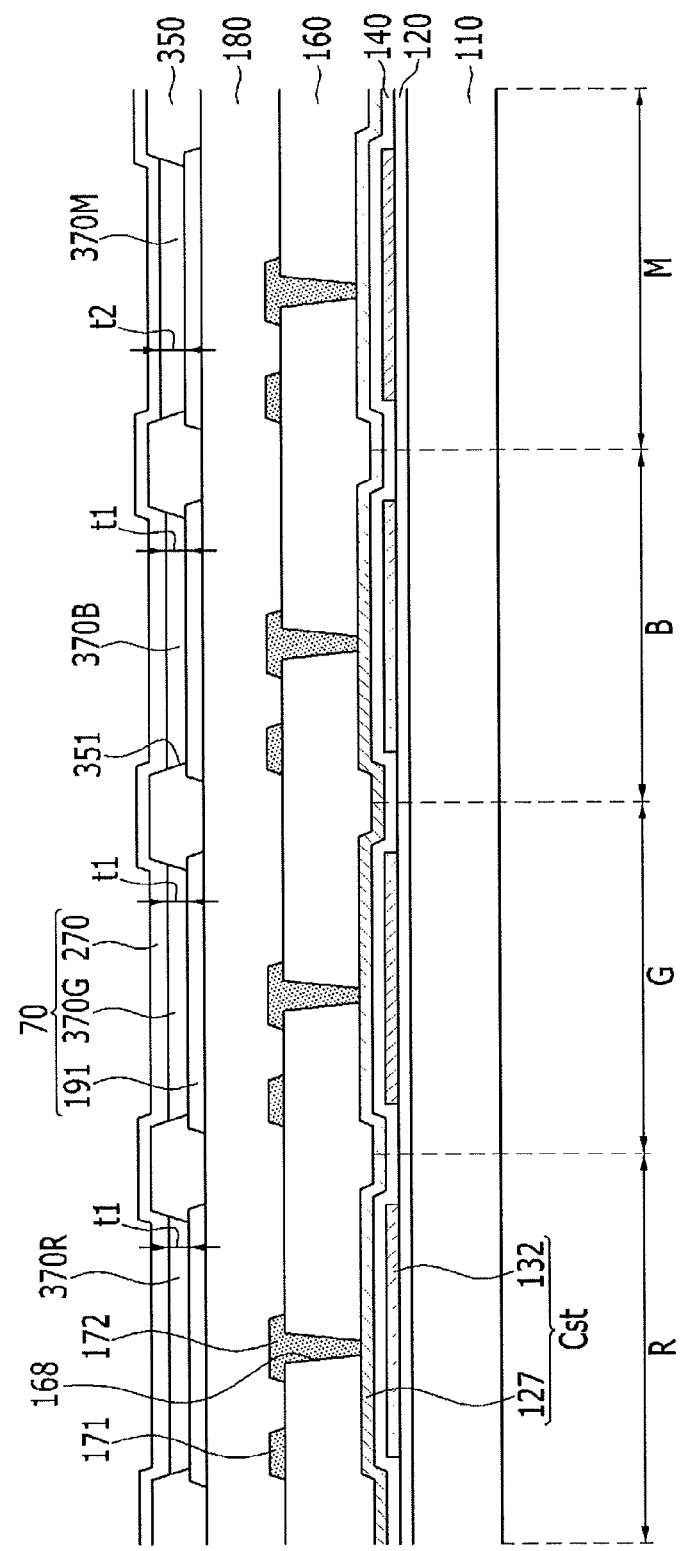
FIG. 6 illustrates a view taken along section line VI-VI in FIG. 3.

FIG. 3 illustrates an example of locations of the thin film transistors and capacitors in four consecutive pixels of the OLED display device. FIG. 4 illustrates a detailed layout of the melatonin control pixel of FIG. 3. FIG. 5 illustrates a cross-sectional view of FIG. 4 taken along line V-V. FIG. 6 illustrates a cross-sectional view of FIG. 3 taken along the line VI-VI.

As shown in FIGS. 3 to 6, a pixel includes the scan signal line 121, the previous scan line 122, the light emission control line 123, and the initialization voltage line 124 formed along a row direction. These lines respectively transmit scan signal Sn, previous scan signal Sn−1, light emission control signal En, and initialization voltage Vint. In addition, the pixel includes data line 171 and driving voltage line 172 crossing the scan line 121, the previous scan line 122, the light emission control line 123, and the initialization voltage line 124. The data line 171 and driving voltage line 172 respectively apply data signal Dm and driving voltage ELVDD to the pixel.

Further, the driving thin film transistor T1, the switching thin film transistor T2, the compensation thin film transistor T3, the initialization thin film transistor T4, the operation control thin film transistor T5, the light emission control thin film transistor T6, the storage capacitor Cst, the boosting capacitor Cb, and an organic light emitting diode 70 are formed in the pixel.

The driving thin film transistor T1, the switching thin film transistor T2, the compensation thin film transistor T3, the initialization thin film transistor T4, the operation control thin film transistor T5, and the light emission control thin film transistor T6 are formed along a semiconductor layer 131. The semiconductor layer 131 may bend in various shapes. The semiconductor layer 131 may be made, for example, of polysilicon or an oxide semiconductor.

The oxide semiconductor may include one of an oxide based on titanium (Ti), hafnium (Hf), zirconium (Zr), aluminum (Al), tantalum (Ta), germanium (Ge), zinc (Zn), gallium (Ga), tin (Sn), or indium (In), such as zinc oxide (ZnO), indium-gallium-zinc oxide (InGaZnO$_4$), indium-zinc oxide (Zn—In—O), zinc-tin oxide (Zn—Sn—O), indium-gallium oxide (In—Ga—O), indium-tin oxide (In—Sn—O), indium-zirconium oxide (In—Zr—O), indium-zirconium-zinc oxide (In—Zr—Zn—O), indium-zirconium-tin oxide (In—Zr—Sn—O), indium-zirconium-gallium oxide (In—Zr—Ga—O), indium-aluminum oxide (In—Al—O), indium-zinc-aluminum oxide (In—Zn—Al—O), indium-tin-aluminum oxide (In—Sn—Al—O), indium-aluminum-gallium oxide (In—Al—Ga—O), indium-tantalum oxide (In—Ta—O), indium-tantalum-zinc oxide (In—Ta—Zn—O), indium-tantalum-tin oxide (In—Ta—Sn—O), indium-tantalum-gallium oxide (In—Ta—Ga—O), indium-germanium oxide (In—Ge—O), indium-germanium-zinc oxide (In—Ge—Zn—O), indium-germanium-tin oxide (In—Ge—Sn—O), indium-germanium gallium oxide (In—Ge—Ga—O), titanium-indium-zinc oxide (Ti—In—Zn—O), and hafnium-indium-zinc oxide (Hf—In—Zn—O) which are complex oxides thereof.

When the semiconductor layer 131 is formed of an oxide semiconductor, an additional protective layer may be added to protect the oxide semiconductor that is weak to external environment conditions, such as high temperatures.

The semiconductor layer 131 includes a channel area in which an impurity may not be doped, a source area, and a drain area. The source and drain areas are formed at respective sides of the channel area and are doped with impurities. The impurity may be changed depending, for example, on the type of transistor, e.g., may be an N-type impurity or a P-type impurity.

The semiconductor layer 131 includes a driving semiconductor layer 131a formed in the driving thin film transistor T1, a switching semiconductor layer 131b formed in the switching thin film transistor T2, a compensation semiconductor layer 131c formed in the compensation thin film transistor T3, an initialization semiconductor layer 131d formed in the initialization thin film transistor T4, an operation control semiconductor layer 131e formed in the operation control thin film transistor T5, and a light emission control semiconductor layer 131f formed in the light emission control thin film transistor T6.

The driving thin film transistor T1 includes the driving semiconductor layer 131a, a driving gate electrode 125a, a driving source electrode 176a, and a driving drain electrode 177a. The driving source electrode 176a corresponds to a driving source area 176a doped with an impurity in the driving semiconductor layer 131a. The driving drain electrode 177a corresponds to a driving drain area 177a doped with an impurity in the driving semiconductor layer 131a. The driving gate electrode 125a overlaps the driving semiconductor layer 131a and is formed with a wider area than the driving semiconductor layer 131a.

The switching thin film transistor T2 includes the switching semiconductor layer 131b, a switching gate electrode 125b, a switching source electrode 176b, and a switching drain electrode 177b. The switching source electrode 176b is a part of the data line 171. The switching drain electrode 177b corresponds to a switching drain area 177b doped with an impurity in the switching semiconductor layer 131b.

The compensation thin film transistor T3 includes compensation semiconductor layer 131c, a compensation gate electrode 125c, a compensation source electrode 176c, and a compensation drain electrode 177c. The compensation source electrode 176c may be doped with an impurity. The compensation drain electrode 177c may be part of a connection member 174.

The initialization thin film transistor T4 includes initialization semiconductor layer 131d, an initialization gate electrode 125d, an initialization source electrode 176d, and an initialization drain electrode 177d.

The operation control thin film transistor T5 includes the operation control semiconductor layer 131e, an operation control gate electrode 125e, an operation control source electrode 176e, and an operation control drain electrode 177e. The light emission control thin film transistor T6 includes the light emission control semiconductor layer 131f, a light emission control gate electrode 125f, a light emission control source electrode 176f, and a light emission control drain electrode 177f.

The storage capacitor Cst may include a first storage capacitor plate 132 and a second storage capacitor plate 127, and a gate insulating layer 140 therebetween. The gate insulating layer 140 may serve as a dielectric material. A storage capacitance may be determined based on the charge stored in the storage capacitor Cst and the voltage between the two storage capacitor plates 132 and 127.

The first storage capacitor plate 132 may be formed in the same layer as the semiconductor layer 131. The second storage capacitor plate 127 may be formed in the same layer as the scan line 121 and the previous scan line 122.

The driving semiconductor layer 131a of the driving thin film transistor T1 connects the switching semiconductor layer 131b and compensation semiconductor layer 131c and the driving control semiconductor layer 131e and light emission control semiconductor layer 131f with each other.

Thus, the driving source electrode 176a is connected to the switching drain electrode 177b and the driving control drain electrode 177e. The driving drain electrode 177a is connected to the compensation drain electrode 177c and the light emission control source electrode 176f.

The first storage capacitor plate 132 of the storage capacitor Cst is connected to the compensation source electrode 176c and the initialization drain electrode 177d, and is connected to the driving gate electrode 125a through the connection member 174. In this case, the connection member 174 may be formed on the same layer as the data line 171. Thus, the connection member 174 is connected to the first storage capacitor plate 132 through a contact hole 166 formed in an interlayer insulating layer 160 and the gate insulating layer 140. The connection member 174 may also be connected to the driving gate electrode 125a through a contact hole 67 formed in the interlayer insulating layer 160. The second storage capacitor plate 127 of the storage capacitor Cst is connected to the common voltage line through a contact hole 168 and is substantially parallel to the scan line 121.

A first boosting capacitor plate 133 of the boosting capacitor Cb may be a portion extended from the first boosting capacitor plate 133. A second boosting capacitor plate 129 may be a portion protruding up and down from the scan line 121. The first boosting capacitor plate 133 may be formed, for example, in the shape of a hammer. The first boosting capacitor plate 133 may include a grip portion 133a that is parallel to the driving voltage line 172 and a head portion 133b formed at an end of the grip portion 133a.

A structure of one embodiment of the OLED display device will now be described. In the following description, a structure of the driving thin film transistor T1, switching thin film transistor T2, and light emission control thin film transistor T6 will specifically be described. The other thin film transistors T3, T4, and T5 may be understood to be substantially the same as the layering structure of thin film transistors T1, T2, and T6.

A buffer layer 120 is formed on a substrate 110. The driving semiconductor layer 131a, the switching semiconductor layer 131b, and the light emission control semiconductor layer 131f are formed on the buffer layer 120. The driving semiconductor layer 131a includes a driving channel area 131a1, the driving source area 176a, and the driving drain area 177a. The driving source area 176a and the driving drain area 177a face each other, with driving channel area 131a1 interposed therebetween. The switching semiconductor layer 131b includes a switching channel area 131b1, the switching source area 132b, and the switching drain area 177b. The switching source area 132b and switching drain area 177b face each other, with the switching channel area 131b1 interposed therebetween. The light emission control transistor T6 includes a light emission control channel area 131f1, the light emission control source area 176f, and the light emission control drain area 133f.

The gate insulation layer 140 may be made, for example, of a silicon nitride ($SiN_x$) or a silicon oxide ($SiO_x$), and may be formed on the switching semiconductor layer 131a, driving semiconductor layer 131b, and light emission control semiconductor layer 131f.

Gate wires 121, 123, 125a, 125b, and 125f including the driving gate electrode 125a, the scan line 121 including the switching gate electrode 125b, and the light emission control line 123 including the light emission control gate electrode 125f may be formed on the gate insulating layer 140.

The interlayer insulating layer 160 may be formed on the gate wires 121, 123, 125a, 125b, and 125f and the gate insulating layer 140. Like the gate insulating layer 140, the interlayer insulating layer 160 may be made of a ceramic-based material, such as but not limited to silicon nitride ($SiN_x$) or silicon oxide ($SiO_x$).

Data line 171, switching source electrode 176b, connection member 174, light emission control drain electrode 177f, and driving voltage line 172 may be formed on the interlayer insulating layer 160.

In addition, light emission control drain electrode 177f may be connected to the light emission control drain area 133f of the light emission control semiconductor layer 131f through a contact hole 72 formed in the gate insulating layer 140 and the interlayer insulating layer 160. The other end of connection member 174 may be connected to the driving gate electrode 125b through the contact hole 67 formed in the interlayer insulating layer 160.

A protective layer 180 covering lines 171, 172, 174, 176b, and 177f is formed on the interlayer insulating layer 160. A pixel electrode 191 may be formed as a first electrode on the protective layer 180. The pixel electrode 191 may be connected to the light emission control drain electrode 177f through a contact hole 181 formed in the protective layer 180.

A barrier rib 350 may be formed at the edge of the pixel electrode 191 and on the protective layer 180. The barrier rib 350 may include a barrier rib opening 351 that exposes the pixel electrode 191. The barrier rib 350 may be made of a resin (e.g., a polyacrylate resin or a polyimide resin) or a silica-based inorganic material.

An organic emission layer 370 is formed on the pixel electrode 191 exposed through the barrier rib opening 351. A common electrode 270 may be formed as a second electrode on the organic emission layer 370. In this way, the organic light emitting diode 70 is formed to include pixel electrode 191, organic emission layer 370, and common electrode 270.

The pixel electrode 191 may serve as an anode (which is a hole injection electrode) and the common electrode 270 may serve as a cathode (which is an electron injection electrode). In other embodiments, the pixel electrode 191 may be a cathode and the common electrode 270 may be an anode. Holes and electrons are injected from the pixel electrode 191 and common electrode 270 into the organic light emitting layer 370. Excitons are formed as the holes and electrons are injected into the organic light emitting layer 370. When the holes and electrons combine, they change from an excited state to a ground state. As a result, the organic light emitting layer 370 emits light.

The organic emission layer 370 may be formed of a low molecular organic material or a high molecular organic material such as poly(3,4-ethylenedioxythiophene) (PEDOT). In addition, the organic emission layer 370 may be formed of a multilayer including one or more of an emission layer, a hole injection layer (HIL), a hole transport layer (HTL), an electron transport layer (ETL), and an electron injection layer (EIL). When the organic emission layer 370 includes all the above-stated layers, the hole injection layer (HIL) may be disposed on the first electrode 191, which serves as a positive electrode. The hole transport layer (HTL), the emission layer, the electron transport layer (ETL), and the electron injection layer (EIL) are sequentially layered on the hole injection layer.

The organic emission layer 370 may include a red organic emission layer 370R, a green organic emission layer 370G, and a blue organic emission layer 370B. The red organic emission layer 370R, the green organic emission layer 370G, and the blue organic emission layer 370B may be formed in a red pixel, a green pixel, and a blue pixel, respectively, to thereby form a color image.

In addition, the organic emission layer 370 may include a melatonin control organic emission layer 370M. This layer may include an emission layer EML that emits light of a melatonin production inhibition wavelength range. The melatonin control organic emission layer 370M is formed in the melatonin control pixel M.

Further, a thickness t2 of the melatonin control organic emission layer 370M may be different from a thickness t1 of one or more of the red organic emission layer 370R, the green organic emission layer 370G, and the blue organic emission layer 370B. That is, a resonance structure may be formed by controlling the thickness of at least one of the emission layer EML of the melatonin control organic emission layer 370M, the hole injection layer, the hole transport layer, the electron transport layer, or the electron injection layer. As a result, the intensity of light of the melatonin production inhibition wavelength range may be maximized or otherwise controlled to be at a predetermined level.

Light of a peak wavelength in the melatonin production inhibition wavelength range (e.g., 414 nm to 514 nm) may be formed by controlling the resonance structure of the melatonin control organic emission layer 370M. This light may have a full width at half maximum (FWHM) of greater than 1 nm and less then 50 nm. This light may be selectively emitted or blocked in the melatonin production inhibition wavelength range.

Figure 7:
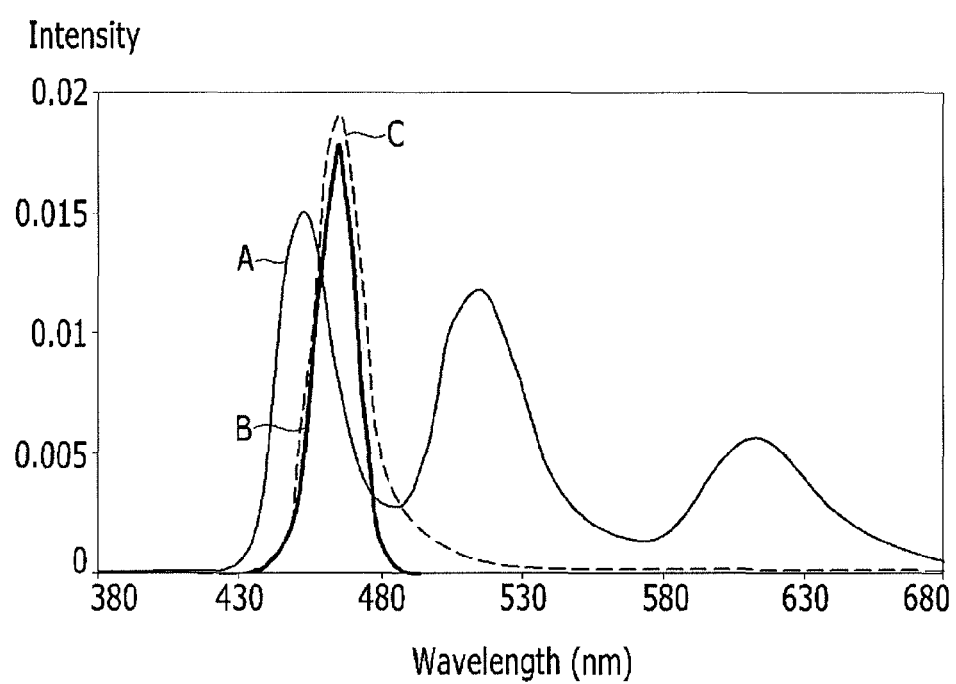
FIG. 7 illustrates an absorption spectrum C of the display device according to one embodiment, an absorption spectrum A of another type of display device, and an example of an absorption spectrum B of a melatonin control cell.

FIG. 7 illustrates an example of an absorption spectrum C of one embodiment of the OLED display device, an absorption spectrum A of another type of OLED display device, and an absorption spectrum B of a melatonin control cell. As shown in FIG. 7, absorption spectrum C is similar to absorption spectrum B of the melatonin control cell. That is, the intensity of light is maximized in a wavelength range of 414 nm to 514 nm, which is the melatonin production inhibition wavelength range.

Therefore, light of the melatonin production inhibition wavelength range is emitted to suppress production of melatonin in the daytime and light of the melatonin production inhibition wavelength range is deliberately blocked in the nighttime to thereby activate biorhythms.

An encapsulation member may be included to protect the organic light emitting diode 70. The encapsulation member may be formed on the common electrode 270, and may be sealed to substrate 110 by a sealant. The encapsulation member may be made, for example, of glass, quartz, ceramic, plastic, metal, or another material. An encapsulation thin film layer may be formed, for example, by depositing an inorganic layer and an organic layer on the common electrode 270 rather than using the sealant.

In accordance with one or more of the aforementioned embodiments, an OLED display is provided to include one or more melatonin control pixels that emit or block light of a melatonin production inhibition wavelength range. The melatonin control pixels may emit light of a melatonin production inhibition wavelength range in the daytime and block light of the melatonin production inhibition wavelength range in the nighttime. As a result, production of melatonin of a viewer mat be blocked in the daytime and may be boosted in the nighttime for control of biorhythms.

In the aforementioned embodiments, the OLED display device is described to have certain structures. However, the OLED display device may have different structures in other embodiments. For example, each pixel of the OLED display may be provided with a plurality of thin film transistors and one or more capacitors. Also, additional wires may be including and/or one or more of the wires that are shown may be omitted or replaced with a different arrangement. Also, in one embodiment, a pixel may be understood to correspond to a minimum unit for displaying light to be included in an image, e.g., a sub-pixel. In other embodiments, a pixel may be understood to be a pixel or a unit different from a minimum unit for displaying light to be included in an image. It is also understood that the display device displays an image based on light emitted from a plurality of pixels.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organic light emitting diode (OLED) display device, comprising:
    a substrate; and
    three color pixels and a melatonin control pixel on the substrate,
    wherein the melatonin control pixel is to emit or block light in a melatonin production inhibition wavelength range, and wherein a thickness of an organic emission layer of the melatonin control pixel is different from a thickness of an organic emission layer of one or more of the three color pixels.

2. The display device as claimed in claim 1, wherein the melatonin production inhibition wavelength range includes about 414 nm to about 514 nm.

3. The display device as claimed in claim 2, wherein light emitted from the melatonin control pixel has a peak in the melatonin production inhibition wavelength range, and has a full width at half maximum of greater than 1 nm and less than 50 nm.

4. The display device as claimed in claim 1, wherein each of the three color pixels and the melatonin control pixel includes:
    thin film transistors on the substrate;
    a first electrode connected to the thin film transistors;
    an organic emission layer on the first electrode; and
    a second electrode on the organic emission layer.

5. The display device as claimed in claim 1, wherein the organic emission layer of the melatonin control pixel is to emit the light in the melatonin production inhibition wavelength range.

6. The display device as claimed in claim 1, wherein the three color pixels are a red pixel, a green pixel, and a blue pixel.

7. A display device, comprising:
    a signal line; and
    a first pixel connected to the signal line and having an organic emission layer with a thickness different from a thickness of an organic emission layer of another pixel, wherein the first pixel is to emit light in a predetermined range during a first time period and is not to emit light in the predetermined range during a second time period during which an image is displayed, wherein the second time period does not overlap the first time period, and wherein the predetermined range is a melatonin production inhibition wavelength range.

8. The display device as claimed in claim 7, wherein:
    the first pixel is to receive a control signal from the signal line, and
    the display device includes a second pixel to emit or not to emit light in the predetermined range based on the control signal.

9. The display device as claimed in claim 7, wherein:
    the first time period is daytime, and
    the second time period is nighttime.

10. The display device as claimed claim 7, further comprising:
    a plurality of second pixels to emit different colors of light during the first and second time periods.

11. The display device as claimed in claim 10, wherein the light emitted from the first pixel has a peak in the melatonin production inhibition wavelength range, and has a full width at half maximum of greater than 1 nm and less than 50 nm.

12. The display device as claimed in claim 10, wherein a sum of light from the first pixel and light from at least one of the second pixels combine to increase inhibition of production of melatonin during the first time period.

13. The display device as claimed in claim 10, wherein at least one of the second pixels is a blue pixel.

14. A display device, comprising:
    a first pixel to emit light; and
    a second pixel to emit light in a predetermined range in a first time period and to not emit light in the predetermined range in a second time period during which the first pixel emits light, wherein the first pixel includes a first organic emission layer having a first thickness and the second pixel includes a second organic emission layer having a second thickness different from the first thickness, and wherein a resonance pattern is formed in the second pixel to emit light in a melatonin production inhibition wavelength range that corresponds to the predetermined range.

15. The display device as claimed in claim 14, wherein:
the first time period is daytime, and
the second time period is nighttime.

16. The display device as claimed in claim 14, wherein the first pixel is to emit blue light.

17. The display device as claimed in claim 14, wherein the first pixel emits light when the second pixel does not emit light in the predetermined range.

18. The display device as claimed in claim 14, wherein the light emitted from the first pixel has a peak in the melatonin production inhibition wavelength range, and has a full width at half maximum of greater than 1 nm and less than 50 nm.

19. The display device as claimed in claim 14, wherein a sum of light from the first pixel and light from the second pixel combines to increase inhibition of production of melatonin in during the first time period.

* * * * *